United States Patent [19]

Takahashi et al.

[11] Patent Number: 5,179,212

[45] Date of Patent: Jan. 12, 1993

[54] PROCESS FOR THE PREPARATION OF 3-PYRROLIDINOLS AND INTERMEDIATES THEREFOR

[75] Inventors: Satomi Takahashi, Kobe; Shigeo Hayashi; Naoaki Taoka, both of Takasago; Noboru Ueyama, Kakogawa, all of Japan

[73] Assignee: Kanegafuchi Chemical Industry Co., Ltd., Osaka, Japan

[21] Appl. No.: 619,974

[22] Filed: Nov. 30, 1990

[30] Foreign Application Priority Data

Dec. 2, 1989 [JP] Japan .................................. 1-313889

[51] Int. Cl.$^5$ .................. C07D 207/24; C07D 207/12
[52] U.S. Cl. ......................................... 548/541; 558/48
[58] Field of Search ........................... 548/541; 558/48

[56] References Cited

U.S. PATENT DOCUMENTS 4,910,320 3/1990 Inoue et al. ......................... 548/541

FOREIGN PATENT DOCUMENTS 0269258 6/1988 European Pat. Off. .
0347818 12/1989 European Pat. Off. .

OTHER PUBLICATIONS

Tetsuo Shiba et al., *The Chemical Society of Japan*, 55, 1982, pp. 899–903, "Synthesis and Stereochemistry of Hypusine, a New Amino Acid in Bovine Brain".

*Primary Examiner*—David B. Springer
*Attorney, Agent, or Firm*—Wegner, Cantor, Mueller & Player

[57] ABSTRACT

3-Pyrrolidinol or its salt is economically produced by cyclizing an aminobutanol derivative of the formula:

$$RSO_2O-CH_2-\underset{\underset{OH}{|}}{CH}-CH_2-CH_2-NH_2$$

wherein R is an alkyl or a substituted or unsubstituted phenyl group, or its salt.

14 Claims, No Drawings

PROCESS FOR THE PREPARATION OF 3-PYRROLIDINOLS AND INTERMEDIATES THEREFOR

BACKGROUND OF THE INVENTION

1. Field of the Invention

The present invention relates to a novel amino butanol derivative and a process for the production of 3-pyrrolidinol from said aminobutanol derivative. More particularly, the present invention relates to a process for the effective and economical production of 3-pyrrolidinol or its salt and an aminobutanol derivative or its salt which is useful as an intermediate in the production of 3-pyrrolidinol.

3-Pyrrolidinol is an important intermediate in the production of a calcium-blocker or δ-lactam antibiotics.

2. Description of the Related Art

For the preparation of 3 pyrrolidinol, following processes are known:

(1) a process comprising hydroxylating a N-substituted-3-pyrroline of the formula:

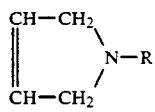
(III)

by hydroboration to obtain a 3-pyrrolidinol derivative of the formula:

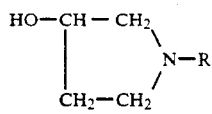
(IV)

(see, for example, J. Org. Chem., 51, 4296 (1986) and Syn. Comm., 13, 1117 (1983)), (2) a process comprising synthesizing 1-benzylmalic acid imide of the formula:

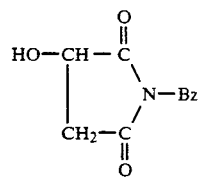
(V)

wherein Bz represents a benzyl group, from malic acid of the formula:

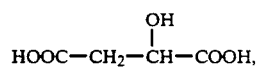
(VI)

and reducing the 1-benzylmalic acid imide (V) to obtain 1-benzyl-3-pyrrolidinol of the formula:

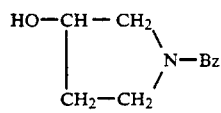
(VII)

wherein Bz is the same as defined above (see Syn. Comm., 15, 587 (1985)), and (3) a process comprising decarboxylating hydroxyproline of the formula:

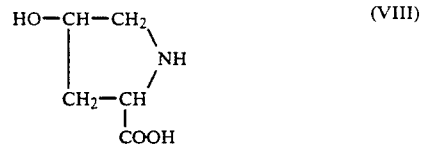
(VIII)

to obtain 3-pyrrolidinol (see Chem. Let., 893 (1986)).

Among the above processes, the process (1) utilizing the hydroboration and the process (2) using malic acid as the starting compound use comparatively expensive reagents such as diborane or lithium aluminum hydride. In the process (2), when optically active malic acid is used as the starting compound, since the compound is partly racemized during cyclization, the product should be subjected to optical resolution to obtain optically pure 3-pyrrolidinol.

The process (3) comprising decarboxylation of hydroxy proline has a drawback that the starting material proline is expensive.

Therefore, none of these three conventional processes is a commercially attractive one.

SUMMARY OF THE INVENTION

One object of the present invention is to provide a process for easily and efficiently producing 3-pyrrolidinol.

Another object of the present invention is to provide a compound which is useful as an intermediate in the production of 3-pyrrolidinol.

According to a first aspect of the present invention there is provided an aminobutanol derivative of the formula:

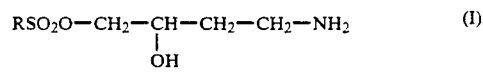
(I)

wherein R is an alkyl group or a substituted or unsubstituted phenyl group, or its salt.

According to a second aspect of the present invention, there is provided a process for the production of 3-pyrrolidinol comprising cyclizing an aminobutanol derivative (I) or its salt under a neutral to basic condition to obtain 3-pyrrolidinol.

According to a third aspect of the present invention, there is provided a process for the production of 3-pyrrolidinol or its salt which comprises steps of:

reducing a 3,4-dihydroxybutyronitrile derivative of the formula:

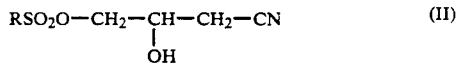
(II)

wherein R is the same as defined above to obtain an aminobutanol derivative (I) or its salt, and cyclizing the aminobutanol derivative (I) or its salt under a neutral to basic condition to obtain 3-pyrrolidinol.

DETAILED DESCRIPTION OF THE INVENTION

In the present specification, R is generally an alkyl group or a substituted or unsubstituted phenyl group.

Examples of the R group is an alkyl group such as a methyl group, an ethyl group, a propyl group and a butyl group, and a phenyl group which may be substituted with a lower alkyl group having 1 to 8 carbon atoms, a halogen atom or an alkoxy group having 2 to 8 carbon atoms. Among them, a tolyl group and a methyl group are preferred from an economical view point.

The aminobutanol derivative (I) or its salt which is used as an intermediate in the production of 3-pyrrolidinol is a novel compound and easily cyclized to form 3 pyrrolidinol stoichiometrically under a neutral to basic condition.

Under a specific condition, the 3,4-dihydroxybutyronitrile derivative (II) can be simultaneously reduced and cyclized to form 3-pyrrolidinol.

When an optically active 3,4-dihydroxybutyronitrile derivative (II) is used, optically active 3-pyrrolidinol can be produced through the aminobutanol derivative (I) with the retention of the optical structure.

The 3,4-dihydroxybutyronitrile derivative (II) which is used as the starting material can be synthesized from 3,4-dihydroxybutyronitrile according to, for example, the following reaction:

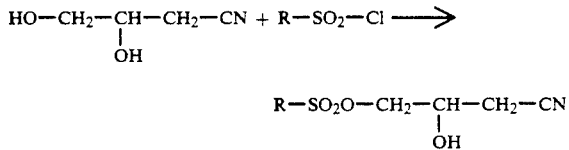

3,4 Dihydroxybutyronitrile can be prepared by cyanating 3-chloro-1,2-propanediol (see J. Am. Chem. Soc., 107, 7008 (1985)). In this preparation, when optically active (R)-3-chloro-1,2-propanediol is used as a starting material, optically active (S)-dihydroxybutyronitile can be obtained. From optically active (S)-dihydroxybutyronitile, optically active (S)-3,4-dihydroxybutyronitile derivative (II) can be easily prepared. Optically active (R)-3-chloro1,2-propanediol is prepared by stereoselective bioresolution of racemic 3-chloro-1,2-propanediol (see Japanese Patent Kokai Publication Nos. 122597/1987, 158494/1987 and 36798/1988).

From L-ascorbic acid or D-sorbitol, an (R)-isomer of 3,4-dihydroxybutyronitrile derivative (II) can be prepared by a multi-step process (see J. Am. Chem. Soc., 102, 6304 (1980)).

The 3,4-dihydroxybutyronitrile derivative (II) is reduced to the aminobutanol derivative (I) by a catalytic reduction under an acidic condition or with a metal hydride The aminobutanol derivative (I) is then cyclized under a neutral or basic condition to obtain 3-pyrrolidinol.

When the 3,4-dihydroxybutyronitrile derivative (II) is reduced under the neutral to basic condition, it is reduced and cyclized to obtain 3-pyrrolidinol. Therefore, 3-pyrrolidinol can be prepared in a single reaction system without isolating the intermediate aminobutanol derivative (I).

When the 3,4-dihydroxybutyronitrile derivative (II) is reduced by the catalytic reduction, any of conventional catalysts may be used. For example, metal catalysts, in particular, palladium catalysts, Raney metal catalysts and platinum catalysts are preferred. The catalysts may be used independently or as a mixture.

As a solvent, any of solvents which are used in conventional catalytic reduction may be used. Preferred examples of the solvent are methanol, ethanol, n-propanol, isopropanol, butanol, water, acetic acid, dioxane, cyclohexane, hexane, toluene, etc. The solvents may be used independently or as a mixture.

In the reduction with the metal hydride, lithium aluminum hydride, lithium boron hydride, borans or cobalt chloride is preferably used. Any of conventionally used solvents may be used. Preferred examples of the solvent are ethyl ether, diglyme, triglyme, tetrahydrofuran, dioxane, methanol, ethanol, n-propanol, isopropanol, etc. The solvents may be used independently or as a mixture.

When the optically active 3,4-dihydroxybutyronitrile derivative (II) ((R)- or (S)-isomer) is reduced under the above condition, the optically active aminobutanol derivative (I) ((R)- or (S)-isomer) can be used without racemization.

The aminobutanol derivative (I) may form a salt with any of suitable organic and inorganic acids. Examples of the salt are hydrochloride, sulfate, acetate, formate, propionate, butyrate, phosphate, etc.

In the cyclization of the aminobutanol derivative (II) to form 3-pyrrolidinol, when the aminobutanol derivative (II) is stirred under the basic condition, any base may be used. Preferred examples of the base are sodium carbonate, sodium hydrogencarbonate, sodium hydroxide, potassium carbonate, potassium hydrogencarbonate, potassium hydroxide, etc. The bases may be used independently or as a mixture.

Any suitable solvent may be used. Preferred examples of the solvent are alcohols (e.g. methanol, ethanol, n-propanol, isopropanol, butanol, etc.), a mixture of such alcohol with water, a mixture of water with an ether (e.g. ethyl ether, tetrahydrofuran, etc.), dimethylformamide (DMF), dimethylsulfoxide (DMSO), etc.

The reaction temperature is from 10° C. to the boiling point of the solvent, preferably from 15° C. to the boiling point of the solvent.

Alternatively, 3-pyrrolidinol can be obtained by stirring the aminobutanol derivative (I) under the neutral condition. In this case, any organic solvent may be used. The reaction temperature may be the same as above.

When the optically active aminobutanol derivative (I) ((R)- or (S)-isomer) is used and cyclized, optically active 3-pyrrolidinol ((R)- or (S)-isomer) is obtained without racemization.

In the production of 3-pyrrolidinol from the 3,4-dihydroxybutyronitrile derivative (II) in one reaction system by successively carrying out the reduction and the cyclization, when the Raney cobalt catalyst is used, the reactions are carried out in the presence of a catalytic amount (for example, 5 to 20 % by weight based on the starting material) of the Raney cobalt catalyst in methanol under nitrogen pressure of from 0.5 to 50 kg/cm$^2$, preferably from 1 to 10 kg/cm$^2$ at a reaction temperature of from 15 to 150° C., preferably from 30 to 110° C. for a reaction time of from 30 minutes to 50 hours, preferably from 1 to 20 hours while stirring. In this case, 3-pyrrolidinol is produced as a main product.

When the Raney nickel is used, the reactions are carried out in the presence of a catalytic amount (for example, 5 to 20 % by weight based on the starting material) of the Raney nickel catalyst in methanol under nitrogen pressure of from 0.5 to 50 kg/cm$^2$, preferably from 1 to 10 kg/cm$^2$ at a reaction temperature of from 15 to 150° C., preferably from 30 to 120° C. for a reaction time of from 30 minutes to 30 hours, preferably from 1 to 20 hours while stirring. In this case, 3-pyrrolidinol is produced as a main product also.

When a palladium/carbon catalyst is used, the reaction conditions are substantially the same as when the Raney cobalt catalyst is used.

When the optically active 3,4-dihydroxybutyronitrile derivative (II) ((R)- or (S)-isomer) is used, optically active 3-pyrrolidinol ((R)- or (S)-isomer) is obtained without racemization.

The produced 3-pyrrolidinol can be isolated by a per se conventional method such as distillation after removing the catalyst and the like by filtration.

3-Pyrrolidinol forms salts with various acids. Examples of the salt are hydrochloride, sulfate, acetate, formate, propionate, butyrate, phosphate, etc.

The present invention will be illustrated by the following Examples.

EXAMPLE 1

Preparation of (R)-3-hydroxy-4-(p-toluenesulfonyloxy)butylamine

To a solution of (R)-3-hydroxy-4-(p-toluenesulfonyloxy)butyronitrile (17.4 g) in methanol (120 ml), 10 wt. % Pd on carbon (3.0 g) and conc. hydrochloric acid (30 ml) were added. The mixture was stirred in a hydrogen atmosphere of 4.0 kg/cm$^2$ at room temperature for 20 hours. After filtrating off the catalyst, the mixture was evaporated under reduced pressure to obtain a crude product, which was purified by silica gel column chromatography (Wako Gel C200, an eluent: methanol/acetone (volume ratio of 3/7) to obtain pure (R)-3-hydroxy-4-(p-toluenesulfonyloxy)butylamine hydrochloride (18.4 g). Yield, 91 %.

$[\alpha]^{20}_D$: +2.89° (c=0.76, 1 N-HCl).

NMR (90 MHz in D$_2$O, internal standard: DDS): δ (ppm)=7.48 and 7.86 (dd, 4 H, J=7 Hz), 4.13 (m, 3 H), 3.21 (t, 2 H), 2.48 (s, 3 H), and 1.85 (m, 2 H).

TLC (silica gel) (ninhydrin color development):
Ethanol/acetic acid =9.1, R$_f$=0.4,
Butanol/acetic acid/water =4/1/1, R$_f$=0.5,
Butanol/acetic acid/water/ethyl acetate =1/1/1/1, R$_f$=0.75.

EXAMPLE 2

Preparation of (R)-3-pyrrolidinol

To a solution of (R)-3 hydroxy 4-(p-toluenesulfonyloxy)butylamine hydrochloride (8.8 g) in methanol 90 ml), sodium carbonate (3.3 g) was added and the mixture was stirred at room temperature for 8 hours. Then, the mixture was filtered, and the filtrate was evaporated under reduced pressure to obtain crude 3 pyrrolidinol. One tenth of the crude 3-pyrrolidinol was dissolved in methylene chloride. To the solution, triethylamine (432 μl) was added, and after cooling to 0° C., benzoyl chloride (360 μl) was added. After stirring for 2 hours, the mixture was evaporated under reduced pressure and purified by silica gel column chromatography (Wako Gel C200, an eluent: ethyl acetate/methanol (volume ratio of 95/5) to obtain pure N-benzoyl-3-pyrrolidinol (438 mg). Yield, 85 %.

NMR (90 MHz in CDCl$_3$, internal standard: TMS): δ (ppm)=2.15 (m, 2 H), 3.45-3.8 (m, 4 H), 4.5 (m, 2 H), and 7.43 (m, 5 H).

IR (CHCl$_3$) 3350, 1600, 1450 and 1100 cm$^{-1}$.

To nine tenths of the crude 3-pyrrolidinol, polyethylene glycol 400 (9 ml) was added and evaporated under reduced pressure to obtain pure (R)-3-pyrrolidinol (1.05 g) at a boiling point of 100° to 120° C./3 mmHg. Yield, 45 %.

NMR (90 MHz in CDCl$_3$, internal standard: TMS): δ (ppm)=1.56-2.17 (m, 2 H), 2.63-3.8 (m, 6 H), 3.8 (br, 1 H), and 4.27-4.47 (m, 1 H).

IR (neat): 3320, 2960, 2900, 1450, 1350, 1075, 990 and 900 cm$^{-1}$.

Through a solution of pure (R)-3-pyrrolidinol in isopropanol, hydrogen chloride gas was bubbled to form (R)3-pyrrolidinol hydrochloride which was isolated by a conventional method. Its specific rotatory power $[\alpha]^{20}_D$ was −7.6° (c=3.8, methanol). This is the same as the literature known value (see Chemistry Letters, 893 (1986)).

EXAMPLE 3

Preparation of (R)-3-pyrrolidinol

To a solution of (R)-3-hydroxy-4-(p-toluenesulfonyloxy)butyronitrile (6.8 g) in methanol (30 ml), Raney cobalt (1.0 g) was added and stirred in a hydrogen atmosphere of 7.0 kg/cm$^2$ at 100° C. for 6 hours. After filtration, the reaction mixture was evaporated reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography (reversed phase column: Nippon Bunko Fine Pack SIL C$_{18-5}$, 230 nm, 23° C., water/acetonitrile=1/1, 1.0 ml/min.) to find that N-benzoyl-3-pyrrolidinol was produced in a yield of 83 %.

The rest of the crude product was dissolved in methanol (50 ml). To the solution, sodium carbonate (3.2 g) was added and stirred at room temperature for 1 hour. After evaporating off methanol, polyethylene glycol 400 (10 ml) was added to the residue and the mixture was evaporated under reduced pressure to obtain pure (R) 3-pyrrolidinol (0.97 g) at a boiling point of 100 to 120° C./3 mmHg. Yield, 42 %.

The obtained compound had the same specific rotary power, NMR spectrum and IR spectrum as those in Example 2.

EXAMPLE 4

Preparation of (R)-3-pyrrolidinol

To a solution of (R)-3-hydroxy-4-(p-toluenesulfonyloxy)butyronitrile (2.61 g) in methanol (15 ml), Raney nickel (350 mg) was added and stirred in a hydrogen atmosphere of 7.0 kg/cm$^2$ at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced in a yield of 76 %.

EXAMPLE 5

Preparation of (R)-3-hydroxy-4-(methanesulfonyloxy)butylamine

To a solution of (R)-3-hydroxy-4-(methanesulfonyloxy)butyronitrile (14.6 g) in methanol (60 ml), 10 wt. % Pd on carbon (2.5 g) and conc. hydrochloric acid (15 ml) were added. The mixture was stirred in a hydrogen atmosphere of 4.0 kg/cm² at room temperature for 8 hours. After filtrating off the catalyst, the mixture was evaporated under reduced pressure to obtain a crude product, which was purified by silica gel column chromatography (Wako Gel C200, an eluent: methanol/acetone (volume ratio of 1/9) to obtain pure (R)-3-hydroxy-4-(methanesulfonyloxy)butylamine hydrochloride (14.4 g). Yield, 80 %.

NMR (90 MHz in D₂O, internal standard: DDS): δ (ppm)=4.3 (m, 3 H), 3.22 (m, 5 H), and 1.93 (m, 2 H).

TLC (silica gel) (ninhydrin color development):
Ethanol/acetic acid=9.1, $R_f$=0.25,
Butanol/acetic acid/water=4/1/1, $R_f$=0.25,
Butanol/acetic acid/water/ethyl acetate=1/1/1/1, $R_f$=0.66.

EXAMPLE 6

Preparation of (R)-3-pyrrolidinol

To a solution of (R)-3-hydroxy-4-(methanesulfonyloxy)butylamine hydrochloride (8.9 g) in methanol (100 ml), sodium carbonate (4.32 g) was added and stirred at room temperature for 8 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 76 %.

To the rest of the crude 3-pyrrolidinol, polyethylene glycol 400 (12 ml) was added, and the mixture was evaporated under reduced pressure to obtain pure (R)-3-pyrrolidinol (1.4 g) at a boiling point of 100 to 120° C./3 mmHg. Yield, 40 %.

The obtained compound had the same specific rotary power, NMR spectrum and IR spectrum as those in Example 2.

EXAMPLE 7

Preparation of (R)-3-pyrrolidinol

To a solution of (R)-3-hydroxy-4-(methanesulfonyloxy)butyronitrile (3.21 g) in methanol (15 ml), Raney cobalt (610 mg) was added and stirred in a hydrogen atmosphere of 7.0 kg/cm² at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 79 %.

The rest of the crude product was dissolved in methanol (27 ml). To the solution, sodium carbonate (2.3 g) was added and stirred at room temperature for 1 hour. After evaporating off methanol, polyethylene glycol 400 (8 ml) was added to the residue and the mixture was evaporated under reduced pressure to obtain pure (R)-3-pyrrolidinol (0.53 g) at a boiling point of 100 to 120° C./3 mmHg. Yield, 34 %.

The obtained compound had the same specific rotary power, NMR spectrum and IR spectrum as those in Example 2.

EXAMPLE 8

Preparation of (R)-3-pyrrolidinol

To a solution of (R)-3-hydroxy-4-(methanesulfonyloxy)butyronitrile (2.92 g) in methanol (15 ml), Raney nickel (570 mg) was added and stirred in a hydrogen atmosphere of 7.0 kg/cm² at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 76 %.

EXAMPLE 9

Preparation of (S)-3-hydroxy-4-(p-toluenesulfonylnyloxy)butylamine

To a solution of (S)-3-hydroxy-4-(p-toluenesulfonyloxy)butyronitrile (17.0 g) in methanol (120 ml), 10 wt. % Pd on carbon (3.0 g) and conc. hydrochloric acid (30 ml) were added. The mixture was stirred in a hydrogen atmosphere of 4. 0 kg/cm² at room temperature for 20 hours. After filtrating off the catalyst, the mixture was evaporated under reduced pressure to obtain a crude product, which was purified by silica gel chromatography (Wako Gel C200, an eluent: methanol/acetone (volume ratio of 3/7) to obtain pure (S)-3-hydroxy-4-(p toluenesulfonyloxy)butylamine hydrochloride (17.5 g). Yield, 89 %.

$[\alpha]^{20}_D$: −2.89° (c=0.76, 1 N-HCl).

The NMR spectrum and $R_f$ values in TLC were the same as in Example 1.

EXAMPLE 10

Preparation of (S) 3-pyrrolidinol

To a solution of . (S) 3-hydroxy 4-(p-toluenesulfonyloxy)butylamine hydrochloride (8.8 g) in methanol (90 ml), sodium carbonate (3.3 g) was added and stirred at room temperature for 8 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl 3 pyrrolidinol was produced at a yield of 84 %.

To rest of the crude 3-pyrrolidinol, polyethylene glycol 400 (10 ml) was added, and the mixture was evaporated under reduced pressure to obtain pure (S)-3-pyrrolidinol (1.20 g) at a boiling point of 100 to 120° C./3 mmHg. Yield, 46 %.

Through a solution of pure (S)-3-pyrrolidinol in isopropanol, hydrogen chloride gas was bubbled to form (S)3-pyrrolidinol hydrochloride which was isolated by a conventional method. Its specific rotatory power $[\alpha]^{20}_D$ was +7.6° (c=3.86, methanol).

The obtained compound had the same NMR spectrum and IR spectrum as those in Example 2.

EXAMPLE 11

Preparation of (S)-3-pyrrolidinol

To a solution of (S)-3-hydroxy-4 (p-toluenesulfonyloxy)butyronitrile (6.80 g) in methanol (30 ml), Raney cobalt (1.0 mg) was added and stirred in a hydrogen atmosphere of 7.0 kg/cm$^2$ at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 84 %.

EXAMPLE 12

Preparation of (S)-3-pyrrolidinol

To a solution of (S)-3-hydroxy-4-(p-toluenesulfonyloxy)butyronitrile (2.60 g) in methanol (15 ml), Raney nickel (350 mg) was added and stirred in a hydrogen atmosphere of 7.0 kg/cm$^2$ at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 78 %.

EXAMPLE 13

Preparation of (S)-3-hydroxy-4-(methanesulfonyloxy)butylamine

To a solution of (S)-3-hydroxy-4-(methanesulfonyloxy)butyronitrile (14.6 g) in methanol (60 ml), 10 wt. % Pd on carbon (2.5 g) and conc. hydrochloric acid (15 ml) were added. The mixture was stirred in a hydrogen atmosphere of 4.0 kg/cm$^2$ at room temperature for 8 hours. After filtrating off the catalyst, the mixture was evaporated under reduced pressure to obtain a crude product, which was purified by silica gel column chromatography (Wako Gel C200, an eluent: methanol/acetone (volume ratio of 1/9) to obtain pure (S)-3-hydroxy-4-(methanesulfonyloxy)butylamine hydrochloride (14.9 g). Yield, 83 %.

The NMR spectrum and the R$_f$ values in TLC were the same as in Example 5.

EXAMPLE 14

Preparation of (S)-3-pyrrolidinol

To a solution of (S)-3-hydroxy-4-(methanesulfonyloxy)butylamine hydrochloride (8.9 g) in methanol (100 ml), sodium carbonate (4.32 g) was added and stirred at room temperature for 8 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 83 %.

EXAMPLE 15

Preparation of (S)-3-pyrrolidinol

To a solution of (S)-3-hydroxy-4 (methanesulfonyloxy)butyronitrile (3.18 g) in methanol (15 ml), Raney cobalt (610 mg) was added and stirred in a hydrogen atmosphere of 7.0 kg/cm$^2$ at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 78 %.

EXAMPLE 16

Preparation of (S)-3-pyrrolidinol

To a solution of (S)-3-hydroxy-4-(methanesulfonyloxy)butyronitrile (2.90 g) in methanol (15 ml), Raney nickel (570 mg) was added and stirred in a hydrogen atmosphere of 7.0 kg/cm$^2$ at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 74 %.

EXAMPLE 17

Preparation of (RS)-3-hydroxy-4-(p-toluenesulfonyloxy)butylamine

To a solution of (RS)-3-hydroxy-4-(p-toluenesulfonyloxy)butyronitrile (17.0 g) in methanol (120 ml), 10 wt. % Pd on carbon (3.0 g) and conc. hydrochloric acid (30 ml) were added. The mixture was stirred in a hydrogen atmosphere of 4.0 kg/cm$^2$ at room temperature for 20 hours. After filtrating off the catalyst, the mixture was evaporated under reduced pressure to obtain a crude product, which was purified by silica gel chromatography (Wako Gel C200, an eluent: methanol/acetone (volume ratio of 3/7) to obtain pure (RS)-3-hydroxy-4-(p-toluenesulfonyloxy)butylamine hydrochloride (18.1 g). Yield, 92 %.

The NMR spectrum and the R$_f$ values in TLC were the same as in Example 1.

EXAMPLE 18

Preparation of (RS) 3-pyrrolidinol

To a solution of (RS)-3-hydroxy-4-(p-toluenesulfonyloxy)butylamine hydrochloride (8.8 g) in methanol (90 ml), sodium carbonate (3.3 g) was added and stirred at room temperature for 8 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl 3-pyrrolidinol was produced at a yield of 81 %.

EXAMPLE 19

Preparation of (RS)-3-pyrrolidinol

To a solution of (RS)-3-hydroxy-4-(p-toluenesulfonyloxy)butyronitrile (5.53 g) in methanol (28 ml), Raney cobalt (1.0 mg) was added and stirred in a hydrogen atmosphere of 7.0 kg/cm² at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 83 %.

EXAMPLE 20

Preparation of (RS)-3-pyrrolidinol

To a solution of (RS) 3-hydroxy-4-(p toluenesulfonyloxy)butyronitrile (2.55 g) in methanol (15 ml), Raney nickel (350 mg) was added and stirred in a hydrogen atmosphere of 7.0 kg/cm² at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 78 %.

EXAMPLE 21

Preparation of (RS)-3-hydroxy-4-(methanesulfonyloxy)butylamine

To a solution of (RS)-3-hydroxy-4-(methanesulfonyloxy)butyronitrile (14.6 g) in methanol (60 ml), 10 wt. % Pd on carbon (2.5 g) and conc. hydrochloric acid (15 ml) were added. The mixture was stirred in a hydrogen atmosphere of 4.0 kg/cm² at room temperature for 8 hours. After filtering off the catalyst, the mixture was evaporated under reduced pressure to obtain a crude product, which was purified by silica gel chromatography (Wako Gel C200, an eluent: methanol/acetone (volume ratio of 1/9) to obtain pure (RS)-3-hydroxy-4-(methanesulfonyloxy)butylamine hydrochloride (15.4 g). Yield, 85 %.

The NMR spectrum and the $R_f$ values in TLC were the same as in Example 5.

EXAMPLE 22

Preparation of (RS)-3-pyrrolidinol

To a solution of (RS)-3-hydroxy-4-(methanesulfonyloxy)butylamine hydrochloride (8.9 g) in methanol (100 ml), sodium carbonate (4.32 g) was added and stirred at room temperature for 8 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 76 %.

EXAMPLE 23

Preparation of (RS)-3-pyrrolidinol

To a solution of (RS)-3-hydroxy-4-(methanesulfonyloxy)butyronitrile (3.10 g) in methanol (15 ml), Raney cobalt (610 mg) was added and stirred in a hydrogen atmosphere of 7.0 kg/cm² at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at a yield of 73 %.

EXAMPLE 24

Preparation of (RS)-3-pyrrolidinol

To a solution of (RS) 3-hydroxy-4-(methanesulfonyloxy)butyronitrile (3.01 g) in methanol (15 ml), Raney nickel (570 mg) was added and stirred in a hydrogen atmosphere of 7.0 kg/cm² at 100° C. for 6 hours. After filtration, the reaction mixture was evaporated under reduced pressure to obtain a crude product. A part of the crude product was dissolved in methylene chloride. To the solution, 2.2 equivalents of triethylamine and 1.1 equivalents of benzoyl chloride were added at 0° C. Then, the solution was analyzed with high performance liquid chromatography in the same manner as in Example 3 to find that N-benzoyl-3-pyrrolidinol was produced at an yield of 70 %.

What is claimed is:

1. An aminobutanol derivative of the formula:

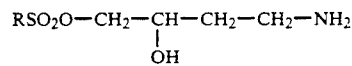

wherein R is selected from the group consisting of methyl, ethyl, propyl, butyl and phenyl the phenyl optionally being substituted with $C_{1-8}$ alkyl, halogen or $C_{2-8}$ alkoxy, or its salt.

2. The aminobutanol derivative according to claim 1, which is optically active.

3. A process for the production of 3-pyrrolidinol or its salt comprising cyclizing an aminobutanol derivative of the formula:

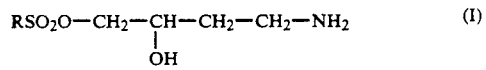

wherein R is R is selected from the group consisting of methyl, ethyl, propyl, butyl and phenyl, the phenyl optionally being substituted with $C_{1-8}$ alkyl, halogen or $C_{2-8}$ alkoyl, and claim claim 6 meters thereto.

4. The process according to claim 3, wherein the cyclization is carried out in the presence of a metal catalyst.

5. The process according to claim 4, wherein said metal catalyst is a Raney metal catalyst.

6. A process for the production of 3-pyrrolidinol or its salt which comprising steps of:

reducing a 3,4-dihydroxybutyronitrile derivative of the formula:

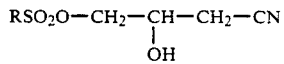

to obtain an aminobutanol derivative of the formula: wherein R is

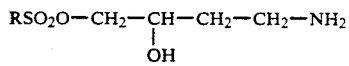

the same as defined above in claim 3 or its salt, and cyclizing the aminobutanol derivative (I) or its salt under a neutral to basic condition to obtain 3-pyrrolidinol.

7. The process according to claim 6, wherein the reducing step and the cyclization step are carried out in a single reaction system without isolation of the aminobutanol derivative (I) or its salt.

8. The process according to claim 6, wherein the reduction or the cyclization is carried out in the presence of a metal catalyst.

9. The process according to claim 8, wherein said metal catalyst is a Raney metal catalyst.

10. The process according to claim 8, wherein said metal catalyst is a palladium base catalyst.

11. The process according to claim 6, wherein an optically active 3,4-dihydroxybutyronitrile derivative is used.

12. The aminobutanol derivative of claim 1, wherein the salt is a salt selected from the group consisting of hydrochloride, sulfate, acetate, formate, propanate, butyrate and phosphate salts.

13. The process of claim 3, wherein the salt is a salt selected from the group consisting of hydrochloride, sulfate, acetate, formate, propanate, butyrate and phosphate salts.

14. The process of claim 6, wherein the salt is a salt selected from the group consisting of hydrochloride, sulfate, acetate, formate, propanate, butyrate and phosphate salts.

* * * * *